(12) United States Patent
Koyama et al.

(10) Patent No.: US 11,035,893 B2
(45) Date of Patent: Jun. 15, 2021

(54) SENSOR DEVICE

(71) Applicant: NIPPON PILLAR PACKING CO., LTD., Osaka (JP)

(72) Inventors: Tatsunari Koyama, Osaka (JP); Akira Nakatsu, Osaka (JP)

(73) Assignee: NIPPON PILLAR PACKING CO., LTD., Osaka (JP)

( * ) Notice: Subject to any disclaimer, the term of this patent is extended or adjusted under 35 U.S.C. 154(b) by 50 days.

(21) Appl. No.: 16/438,509

(22) Filed: Jun. 12, 2019

(65) Prior Publication Data

US 2020/0003813 A1 Jan. 2, 2020

(30) Foreign Application Priority Data

Jun. 28, 2018 (JP) .............................. JP2018-123380

(51) Int. Cl.
| | | |
|---|---|---|
| *G01R 27/08* | (2006.01) | |
| *G01N 33/28* | (2006.01) | |
| *G01N 27/22* | (2006.01) | |
| *G01N 11/00* | (2006.01) | |

(52) U.S. Cl.
CPC ............ *G01R 27/08* (2013.01); *G01N 27/228* (2013.01); *G01N 33/2888* (2013.01); *G01N 2011/0066* (2013.01)

(58) Field of Classification Search
CPC ...... G01R 27/02; G01R 27/08; G01R 27/228; G01N 2011/0066
See application file for complete search history.

(56) References Cited

U.S. PATENT DOCUMENTS

| | | | | |
|---|---|---|---|---|
| 7,043,402 | B2 * | 5/2006 | Phillips ................... | G01N 27/02 324/600 |
| 2009/0315574 | A1 * | 12/2009 | Akiyama ................ | G01N 27/02 324/698 |
| 2010/0180663 | A1 * | 7/2010 | Sun ....................... | G01N 33/2888 73/1.02 |
| 2013/0068015 | A1 * | 3/2013 | Sinha ..................... | G01F 23/268 73/304 C |
| 2014/0375321 | A1 * | 12/2014 | Ikeya ..................... | G01N 27/02 324/324 |
| 2015/0075268 | A1 * | 3/2015 | Qi ......................... | G01N 33/2888 73/114.55 |
| 2018/0059049 | A1 * | 3/2018 | Takizawa ............. | A61B 5/14517 |
| 2019/0064092 | A1 * | 2/2019 | Zhang .................... | G01M 3/16 |
| 2019/0086253 | A1 * | 3/2019 | Ihle ....................... | G01F 23/0061 |

FOREIGN PATENT DOCUMENTS

JP 2009002693 A 1/2009

* cited by examiner

*Primary Examiner* — Dominic E Hawkins
(74) *Attorney, Agent, or Firm* — Kilyk & Bowersox, P.L.L.C.

(57) ABSTRACT

The present invention intends to provide a liquid sensor device that achieves both the improvement of durability and the improvement of property determination accuracy. The liquid sensor device includes: an electrode pair 22 that is formed on a sensor board 2 and covered by an insulating protective film 201; a resistance measurement part 302 that supplies AC current to the electrode pair 22 to measure the resistance value of oil 4; a parasitic capacitance storage part 304 that holds the parasitic capacitance Cs of the electrode pair 22; and a property determination part 313 that, on the basis of the resistance value R1 and the parasitic capacitance Cs, determines the deterioration of the oil 4.

12 Claims, 12 Drawing Sheets

SENSOR DEVICE

TECHNICAL FIELD

The present invention relates to a sensor device, and in more detail, to a sensor device that measures the resistance value of a medium such as liquid to determine a property state of the medium.

BACKGROUND ART

In general, when the properties of a liquid are changed, such as composition and characteristics, the dielectric constant and resistivity of the liquid correspondingly change in many cases. However, what influence is exerted on the dielectric constant or the resistivity is different depending on the type of a target liquid or a property of interest. For example, after a long-term use, engine oil for vehicles is deteriorated due to the interfusion of foreign substance such as soot to reduce resistivity, and therefore it is conceivable that the deterioration can be determined by measuring the resistance of the engine oil.

For example, in the past, an oil deterioration detector adapted to electrically detect the deterioration of oil has been known (Patent Literature 1). This oil deterioration detector detects the deterioration of the oil by arranging two electrodes in an engine oil flow path and measuring the conductivity and dielectric constant of the oil.

When measuring the electrical characteristics of a liquid with an electrode pair immersed in the liquid, there has been a problem that the electrode pair is deteriorated due to corrosion. Specifically, when measuring the resistance of the liquid using an electrode pair made of copper, there has been a problem that the electrode pair in direct contact with the liquid is corroded to make it difficult to ensure the durability of the detector.

Also, in order to prevent the corrosion of the electrode pair, it is conceivable to form the electrode pair using an electrically conductive material having corrosion resistance, such as carbon nanotubes or diamond-like carbon. However, there has been a problem that manufacturing cost is significantly increased. Further, it is also conceivable to prevent the corrosion by gold-plating the electrode pair. However, there has still been a problem of increased manufacturing cost.

CITATION LIST

Patent Literatures

Patent Literature 1: Japanese Unexamined Patent Application Publication No. 2009-02693

SUMMARY OF INVENTION

Technical Problem

The present invention has been made in consideration of the above situations and intends to provide a sensor device that measures the resistance value of a medium such as a liquid to determine the properties of the medium. Also, the present invention intends to improve the durability of the sensor device. Further, the present invention intends to suppress the manufacturing cost of the sensor device and provide the sensor device at low cost.

In particular, the present invention intends to provide a sensor device having both improved durability and improved property determination accuracy. Further, the present invention intends to provide the sensor device that achieves the improvement of durability and the improvement of property determination accuracy without significantly increasing manufacturing cost.

Solution to Problem

A sensor device according to a first aspect of the present invention includes: aa first electrode pair that is formed on a board and covered by an insulating protective film; a resistance measurement part that supplies AC current to the first electrode pair to measure the resistance value of a medium around the first electrode pair; a storage part that holds the parasitic capacitance of the first electrode pair; and a property determination part that, on the basis of the resistance value and the parasitic capacitance, determines a property of the medium.

By covering the first electrode pair for measuring the resistance value of the medium with the insulating protective film, the corrosion of the first electrode pair can be prevented to improve the durability of the device without significantly increasing manufacturing cost. Also, by supplying the AC current to the first electrode pair covered by the insulating protective film to measure the resistance value of the medium around the first electrode pair, the property of the medium can be determined without impairing the durability. Further, by determining the property of the medium on a basis of the resistance value and parasitic capacitance of the first electrode pair, the property determination accuracy of the medium can be improved. Accordingly, employing the above configuration makes it possible to achieve both the improvement of the durability and the improvement of the property determination accuracy while suppressing manufacturing cost.

A sensor device according to a second aspect of the present invention is, in addition to the above configuration, configured to further include a measurement error correction part that, on the basis of the parasitic capacitance, corrects a measurement error of the resistance value, in which the property determination part determines the property of the medium on the basis of the resistance value after the correction.

Employing such a configuration makes it possible to, when measuring the resistance value of the medium around the first electrode pair using the AC current, suppress the influence of the parasitic capacitance of the first electrode pair to accurately obtain the resistance value of the medium. Accordingly, the property determination accuracy of the medium can be improved.

A sensor device according to a third aspect of the present invention is, in addition to the above configuration, configured such that the resistance measurement part measures the impedance of the first electrode pair at the time of supplying AC current having a frequency of 5 kHz or less.

Employing the above configuration makes it possible to suppress the influence of the capacitance of the medium around the first electrode pair on the impedance of the first electrode pair. For this reason, by measuring the impedance of the first electrode pair at the time of supplying the AC current, the resistance value of the medium around the first electrode pair can be accurately obtained.

A sensor device according to a fourth aspect of the present invention is, in addition to the above configuration, configured such that the parasitic capacitance has a value measured as the impedance of the first electrode pair at the time of supplying the AC current to the first electrode pair that is not close to the medium.

Employing such a configuration makes it possible to correct the measured value of the resistance using the parasitic capacitance of the first electrode pair, which is related to the resistance value measurement and accurate. For this reason, the influence of the parasitic capacitance of the first electrode pair on the measured value of the resistance can be effectively suppressed, and thereby the resistance value of the medium around the first electrode pair can be further accurately obtained.

A sensor device according to a fifth aspect of the present invention in addition to the above configuration, configured to further include a medium container tank in which the board is arranged; a capacitance measurement part that supplies AC current having a first frequency to said first electrode pair to measure capacitance of said first electrode pair; a medium amount detection part that, on a basis of the capacitance measured by said capacitance measurement part, detects a medium amount in said container tank; and a medium amount compensation part that, on a basis of said medium amount, corrects said resistance value; in which said first electrode pair extends in a direction intersecting with a horizontal direction; said resistance measurement part supplies AC current having a second frequency different from the first frequency to said first electrode pair to measure a resistance value of a medium around the first electrode pair; and said property determination part determines a property of said medium on a basis of said resistance value after the correction and said parasitic capacitance.

Employing such a configuration makes it possible, by using the same electrode pair, to measure the capacitance of the electrode pair to detect the medium amount as well as to measure the resistance value of the medium around the electrode pair to determine the property of the medium. Accordingly, the property of the medium can also be determined using the board for detecting the medium amount.

A sensor device according to a sixth aspect of the present invention in addition to the above configuration, configured to further include a medium container tank in which the board is arranged; a second electrode pair that is formed on the board, arranged above the first electrode pair, and extends in a direction intersecting with a horizontal direction; a capacitance measurement part that measures capacitance of said second electrode pair; and a medium amount detection part that, on a basis of the capacitance measured by said capacitance measurement part, detects a medium amount in said container tank; in which said protective film covers said first electrode pair and said second electrode pair; said resistance measurement part supplies AC current to said first electrode pair to measure a resistance value of a medium around said first electrode pair; and said storage part holds parasitic capacitance of said first electrode pair.

Employing such a configuration makes it possible to form on the same board the first electrode pair for determining the property of the medium and the second electrode pair for detecting the medium amount, and cover the first electrode pair and the second electrode pair with the same insulating protective film. For this reason, the durability of the first and second electrode pairs can be improved without increasing manufacturing cost.

A sensor device according to a seventh aspect of the present invention is, in addition to the above configuration, configured to further include a measurement error correction part that, on the basis of the parasitic capacitance, corrects a measurement error of the resistance value, in which the property determination part determines the property of the medium on the basis of the resistance value after the correction.

Employing such a configuration makes it possible to, when measuring the resistance value of the medium around the first electrode pair using the AC current, suppress the influence of the parasitic capacitance of the first electrode pair to accurately obtain the resistance value of the medium. Accordingly, the property determination accuracy of the medium can be improved.

A sensor device according to an eighth aspect of the present invention is, in addition to the above configuration, configured to include a temperature measurement part that measures the temperature of the board, and a temperature compensation part that, on the basis of the temperature, corrects the resistance value, in which the property determination part determines the property of the medium on the basis of the resistance value after the correction.

Employing such a configuration enables the influence of the temperature characteristics of the resistance of the medium to be suppressed by measuring the temperature of the medium and correcting the resistance value of the medium and the property determination accuracy of the medium to be improved.

A sensor device according to a ninth aspect of the present invention is, in addition to the above configuration, configured such that the temperature measurement part obtains the temperature of the board by measuring the resistance value of an electrode formed on the board.

Employing such a configuration makes it possible to measure the temperature only with the electrode on the board without using a temperature measuring element such as a thermistor. For this reason, manufacturing cost can be suppressed.

A sensor device according to a tenth aspect of the present invention is, in addition to the above configuration, configured such that the electrode is covered by the protective film Employing such a configuration makes it possible to prevent the corrosion of the electrode for temperature measurement to improve the durability of the device without significantly increasing manufacturing cost.

A sensor device according to an eleventh aspect of the present invention is, in addition to the above configuration, configured such that the medium is liquid, and the property determination part determines the deterioration state of the liquid.

A sensor device according to a twelfth aspect of the present invention is, in addition to the above configuration, configured such that the liquid is oil, and the property determination part determines the deterioration state of the oil.

Advantageous Effects of Invention

According to the present invention, a sensor device that measures the resistance value of a medium such as a liquid and determines the properties of the medium can be provided. Also, the durability of the sensor device can be improved. Further, the manufacturing cost of the sensor device can be suppressed to make it possible to provide it at low cost.

In particular, a sensor device that achieves both the improvement of durability and the improvement of property determination accuracy can be provided. Further, the sensor device having improved durability and improved property

DESCRIPTION OF EMBODIMENTS

In each of the following embodiments, as an example of a sensor device that detects the amount and property of a medium contained in a tank, an oil sensor device that detects the liquid amount and deterioration state of oil contained in an oil tank will be described. Note that the oil sensor device described as each of the embodiments is exemplified, and the present invention is not limited only to a specific configuration described in each of the embodiments.

First Embodiment

Figure 1:
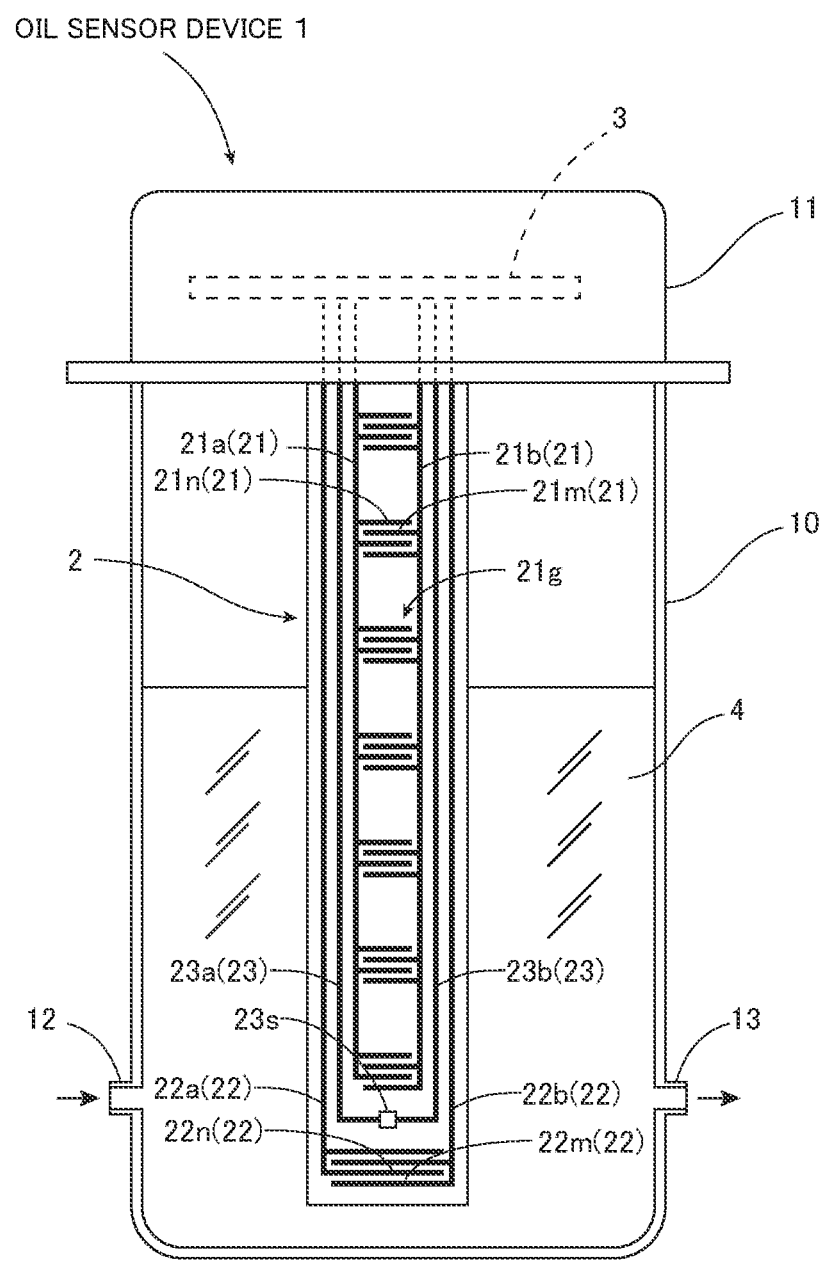
FIG. 1 is a diagram illustrating an example of an oil tank 10 in which an oil sensor device 1 according to a first embodiment of the present invention is attached.

FIG. 1 is a diagram illustrating an example of an oil tank 10 in which an oil sensor device 1 according to a first embodiment of the preset invention is attached. The oil sensor device 1 is a device adapted to detect the liquid amount and deterioration state of oil 4 in the oil tank 10 and configured to include a sensor board 2 and a control circuit 3.

(A1) Oil Tank 10

The oil tank 10 is a container for containing the oil 4, and for example, an oil tank connected to a circulation path of engine oil for vehicles. The oil tank 10 includes an inflow port 12 and an outflow port 13, and the oil 4 supplied from the outflow port 13 to the oil circulation path returns into the oil tank 10 through the inflow path 12 after passing through an engine and an oil filter. The oil tank 10 may be an independent container for storing the oil 4. Also, as long as the liquid amount and deterioration state of the oil 4 is stable enough to be measurable at the time of measurement, the oil tank 10 may be a container from which and into which part of the oil 4 as a measurement target flows.

(A2) Tank Cover 11

The tank cover 11 is a cover for closing the upper opening of the oil tank 10, and attached with the oil sensor device 1. The lower surface side of the tank cover 11 is attached with the sensor board 2, and in a casing on the upper surface side of the tank cover 11, the control circuit 3 is contained.

(A3) Sensor Board 2

The sensor board 2 is a board arranged in the oil tank 10, and one principal surface thereof is provided with an electrode pair 21, an electrode pair 22, an electrode pair 23, and a thermistor 23s, whereas the other principal surface is provided with a ground plate 25. The liquid amount and deterioration state of the oil 4 can be detected by immersing the sensor board 2 in the oil 4. The sensor board 2 has an elongated rectangular shape, and is arranged with the longer direction thereof intersecting with the horizontal direction. The illustrated sensor board 2 extends vertically downward with the upper end thereof fixed to the tank cover 11, and the lower end thereof is arranged near the bottom part of the oil tank 10.

(A4) Control Circuit 3

The control circuit 3 is an electric circuit for controlling the sensor board 2, and arranged outside the oil tank 10. The control circuit 3 is configured to include an unillustrated power supply circuit, a DC converter, a microprocessor, and the like, and connected with the electrode pairs 21 to 23 and the ground plate 25 on the sensor board 2.

Figure 2:
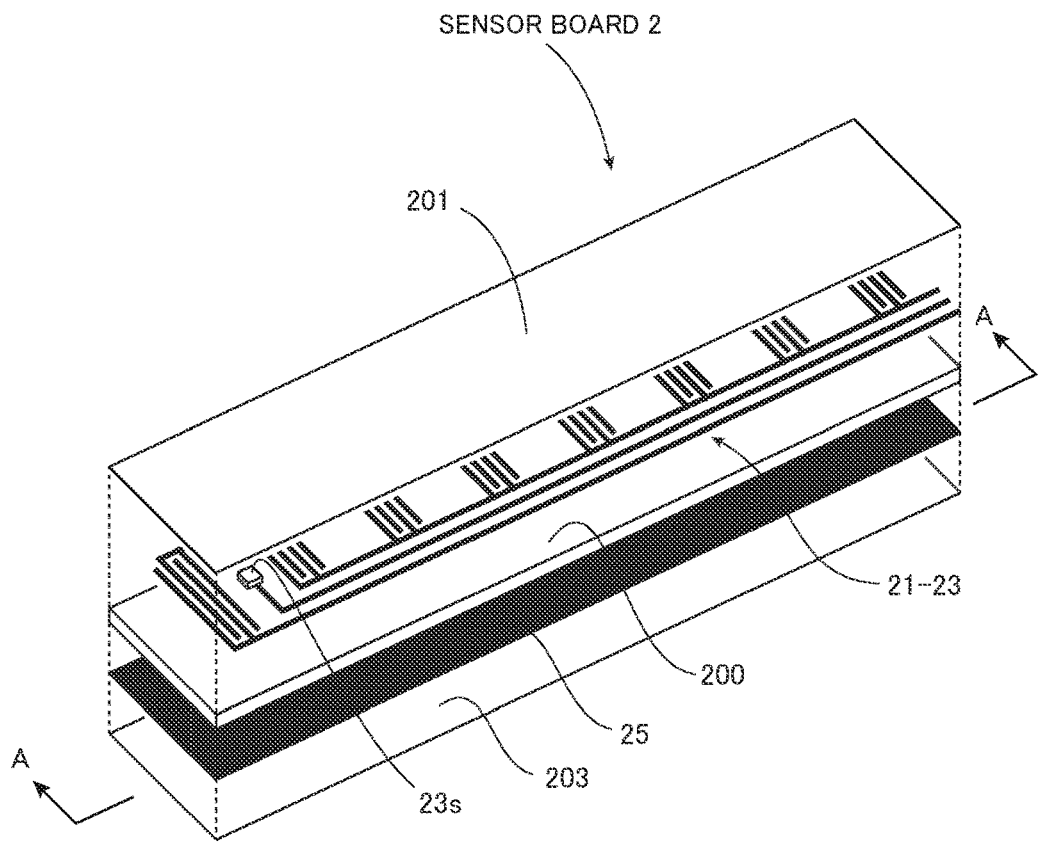
FIG. 2 is a development perspective view illustrating the structure of a sensor board 2 in FIG. 1.
Figure 3:
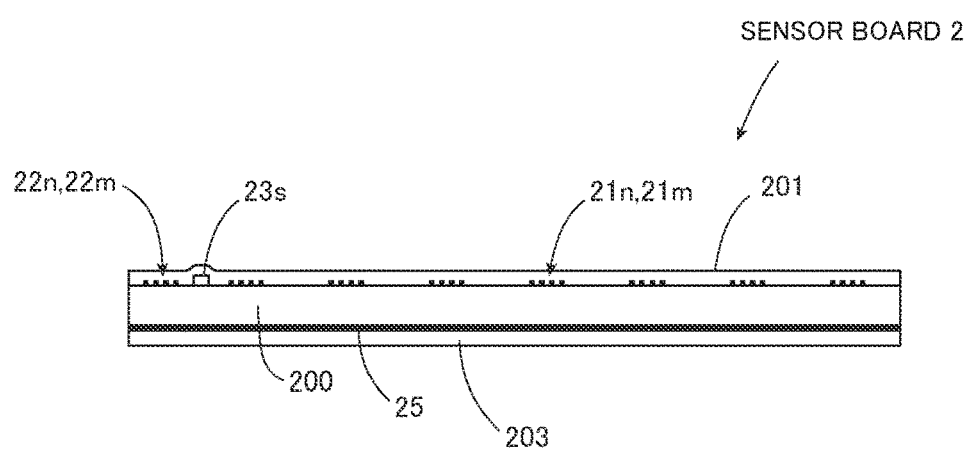
FIG. 3 is a cross-sectional view when cutting the sensor board 2 along an A-A section line in FIG. 2.

FIGS. 2 and 3 are views illustrating a configuration example of the sensor board 2 in FIG. 1. FIG. 2 is a development perspective view illustrating the structure of the sensor board 2. FIG. 3 is a cross-sectional view when cutting the sensor board 2 along an A-A section line in FIG. 2. The configuration of the sensor board 2 will be described here in more detail with reference to FIGS. 1 to 3. The sensor board 2 is configured to include a base material 200, a protective film 201, the electrode pairs 21 to 23, the thermistor 23s, the ground plate 25, and a protective film 203.

(B1) Base Material 200

The base material 200 is made of a dielectric material processed in an elongated rectangular flat-plate shape and having corrosion resistance, such as a fluorine resin. On one principal surface (hereinafter referred to as a first surface) of the base material 200, the electrode pairs 21 to 23 and the thermistor 23s are provided. The electrode pairs 21 to 23 are formed as a patterned electrically conductive metal layer. For example, the electrode pairs 21 to 23 having desired patterns are formed by etching copper foil put on the base material 200, and then the thermistor 23s is soldered. On the other principal surface (hereinafter referred to as a second surface) of the base material 200, the ground plate 25 is provided. The ground plate 25 is formed as an electrically conductive metal layer covering the entire surface of the base material 200. For example, the ground plate 25 is made of copper foil put on the base material 200.

(B2) Protective Film 201

The protective film 201 is a film formed on the first surface of the base material 200, and made of a dielectric material having corrosion resistance, such as a fluorine resin. The protective film 201 is formed on the entire first surface of the base material 200, and covers the electrode pairs 21 to 23 and the thermistor 23s. For this reason, the electrode pairs 21 to 23 and the thermistor 23s are sealed by the base material 200 and the protective film 201 and do not contact with the oil 4 or air, and therefore the electrode pairs 21 to 23 and the thermistor 23s can be prevent from being deteriorated and damaged by corrosion or the like. Also, by covering all the parts on the sensor board 2 with the same protective film 201, manufacturing cost can be suppressed to obtain the sensor device 1 at low cost.

(B3) Electrode Pair 21

The electrode pair 21 is an electrode pair used to detect the liquid level height of the oil 4, and consists of two electrodes 21a and 21b. The electrodes 21a and 21b respectively include two or more opposite elements 21n and 21m.

The electrodes 21a and 21b both have an elongated shape having a substantially uniform width, and extend mutually parallel along the longer direction of the base material 200, and one ends thereof are connected to the control circuit 3. That is, the electrodes 21a and 21b both have a shape extending in a direction intersecting with the horizontal direction, for example, in the vertical direction, and the upper ends thereof are connected to the control circuit 3.

The opposite elements 21n and 21m all have an elongated shape having a substantially uniform width, extend in the shorter direction of the base material 200, and are closely arranged mutually parallel. The electrode 21a is connected with the two or more opposite elements 21n, and the electrode 21b is connected with the two or more opposite elements 21m. Between the electrodes 21a and 21b, three or more opposite elements 21n and 21m are alternately arrayed along the longer direction of the base material 200, and pairs of adjacently arranged opposite elements 21n and 21m respectively form electrode pairs.

When the liquid amount of the oil 4 changes, the liquid level of the oil 4 moves in the vertical direction, and the number of the opposite elements 21n and 21m immersed in the oil 4 is changed depending on the liquid level height of the oil 4. The capacitance between adjacent opposite elements 21n and 21m is significantly changed depending on whether the opposite elements 21n and 21m are present in air or in the oil. For this reason, by measuring the capacitance of the electrode pair 21, the liquid level height of the oil 4 can be measured.

In the case of the electrode pair 21 in the diagram, the two or more opposite elements 21n and 21m closely arranged in the vertical direction form an opposite element group 21g, and two or more opposite element groups 21g are arrayed in the vertical direction at intervals wider than the gap between adjacent opposite elements 21n and 21m. Employing such a configuration makes it possible to discretely detect the liquid level height. In addition, if all the opposite elements 21n and 21m are closely arranged and the electrode pair 21 is configured to have only one opposite element group 21g, the liquid level height can be continuously detected.

(B4) Electrode Pair 22

The electrode pair 22 is an electrode pair used to determine the deterioration state of the oil 4, and consists of two electrodes 22a and 22b. The electrodes 22a and 22b respectively include one or more opposite elements 22n and 22m.

The electrodes 22a and 22b both have an elongated shape having a substantially uniform width, and extend mutually parallel along the longer direction of the base material 200, and one ends thereof are connected to the control circuit 3. That is, the electrodes 22a and 22b both have a shape extending in a direction intersecting with the horizontal direction, for example, in the vertical direction, and the upper ends thereof are connected to the control circuit 3.

The opposite elements 22n and 22m all have an elongated shape having a substantially uniform width, extend in the shorter direction of the base material 200, and are closely arranged mutually parallel. The electrode 22a is connected with the one or more opposite elements 22n, and the electrode 22b is connected with the one or more opposite elements 22m. When three or more opposite elements 22n and 22m are arranged, the opposite elements 22n and 22m are alternately arrayed between the electrodes 22a and 22b, and adjacent opposite elements 22n and 22m respectively form an electrode pair. Also, the opposite elements 22n and 22m are arranged downward of the opposite elements 21n and 21m, and desirably arranged below the thermistor 23s. In addition, the opposite elements 22n and 22m may be arranged above the thermistor 23s.

When the oil 4 is deteriorated after a long-term use, the resistivity of it reduces. For this reason, by measuring the resistance value of the electrode pair 22 with the opposite elements 22n and 22m immersed in the oil 4, the deterioration state of the oil 4 can be determined. However, since the electrode pair 22 is covered with the protective film 201, DC resistance cannot be measured. For this reason, the electrode pair 22 has to be supplied with AC current to measure the resistance of the oil 4.

(B5) Electrode Pair 23

The electrode pair 23 consists of two electrodes 23a and 23b. The electrodes 23a and 23b are respectively connected to the terminals of the thermistor 23s, and therefore by measuring the resistance of the electrode pair 23, the temperature of the sensor board 2 can be measured.

The electrodes 23a and 23b both have an elongated shape having a substantially uniform width, and extend mutually parallel along the longer direction of the base material 200, and the upper ends thereof are connected to the control circuit 3. The thermistor 23s is a well-known temperature detecting element whose resistance value has a relatively large temperature characteristic, and for example, a surface mounting element is attached on the base material 200. The temperature of the sensor board 2 is substantially equal to the temperature of the oil 4 around the sensor board 2, and therefore by measuring the resistance of the electrode pair 23, the temperature of the oil 4 can be acquired. When the thermistor 23s is immersed in the oil 4, the temperature of the oil 4 can be more accurately measured, and therefore the thermistor 23s is arranged below the opposite elements 21n and 21m.

(B6) Ground Plate 25

The ground plate 25 is a ground layer formed on the entire second surface of the base material 200, and connected to the ground of the control circuit 3. Arranging the ground plate 25 in parallel with the electrode pairs 21 to 23 across the base material 200 makes it possible to stabilize the potentials of the electrode pairs 21 to 23 and improve anti-noise characteristics.

(B7) Protective Film 203

The protective film 203 is a film formed on the second surface of the base material 200, and made of a dielectric material having corrosion resistance, such as a fluorine resin. The protective film 203 is formed on the entire second surface of the base material 200, and covers the ground plate 25. For this reason, the ground plate 25 is sealed by the base material 200 and the protective film 203 and does not contact with the oil 4 or air, and therefore the ground plate 25 can be prevent from being deteriorated and damaged by corrosion or the like. In addition, the ground plate 25 and the protective film 203 are provided as needed, and can also be omitted.

(C1) Method for Detecting Liquid Amount of Oil

Figure 4:
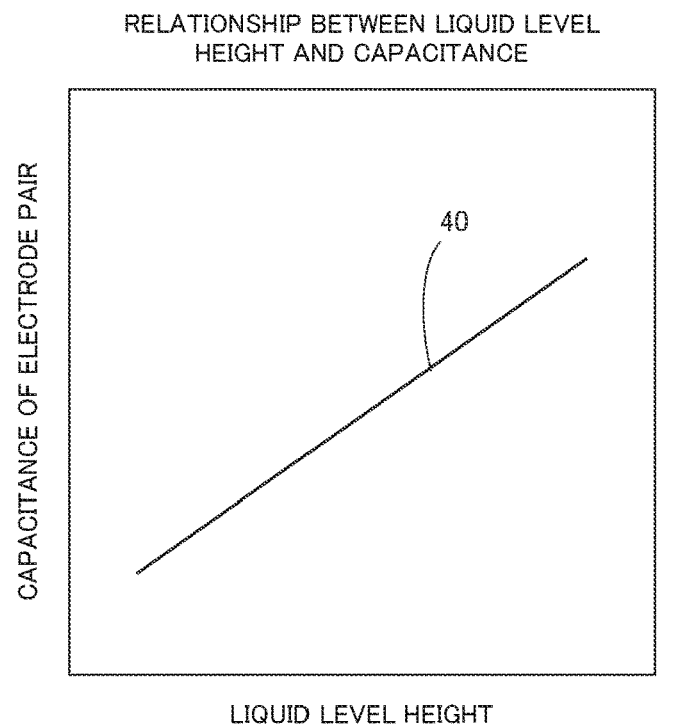
FIG. 4 is a diagram illustrating an example of the relationship between liquid level height and the capacitance of an electrode pair 21.

FIG. 4 is a diagram illustrating an example of the relationship between the liquid level height of the oil 4 and the capacitance of the electrode pair 21. This diagram is one represented with the liquid level height of the oil 4 in the oil tank 10 taken as the horizontal axis and the capacitance of the electrode pair 21 taken as the vertical axis. A characteristic 40 in the diagram exhibits an upward-sloping straight line. That is, it turns out that the capacitance of the electrode pair 21 increases corresponding to the liquid level height of the oil 4, and both have a substantially linear relationship. In addition, when the electrode pair 21 is configured to discretely measure the liquid level height of the oil 4, the measured capacitance of the electrode pair 21 exhibits a characteristic obtained by changing the straight line in FIG. 4 to the stepwise shape.

Since the electrode pair 21 extends in the vertical direction and the many opposite elements 21$n$ and 21$m$ are also arrayed in the vertical direction, the rise of the liquid level height increases the number of opposite elements 21$n$ and 21$m$ immersed in the oil 4. For this reason, the rise of the liquid level height also monotonously increases the capacitance of the electrode pair 21, thus obtaining the characteristic as illustrated in the diagram. Accordingly, as long as the capacitance of the electrode pair 21 can be measured, the liquid level height can be obtained, and the liquid amount of the oil 4 in the oil tank 10 can be detected.

(C2) Method for Detecting Deterioration State of Oil

Figure 5:
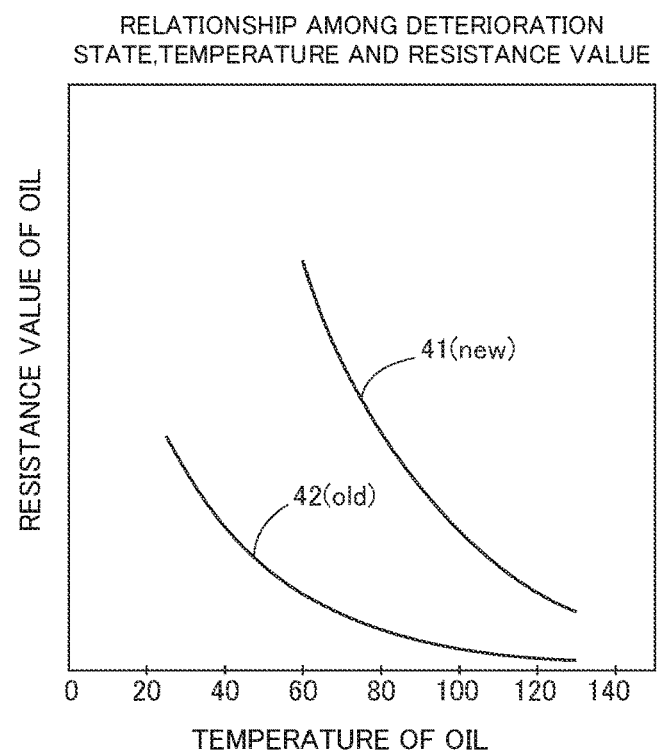
FIG. 5 is a diagram illustrating an example of the relationship among the deterioration state, temperature, and resistance value of oil 4.

FIG. 5 is a diagram illustrating an example of the relationship among the deterioration state, temperature, and resistance value of the oil 4. This diagram is one represented with the temperature of the oil 4 taken as the horizontal axis and the resistance value of the oil 4 taken as the vertical axis. The resistance value of the oil 4 is a value measured using the electrode pair 22, and shows the resistance value of the oil 4 around the opposite elements 22$n$ and 22$m$. Also, a characteristic 41 in the diagram is a characteristic of the oil 4 that is unused and not deteriorated, whereas a characteristic 42 in the diagram is a characteristic of the oil 4 that is used and deteriorated.

When comparing the characteristics 41 and 42, it turns out that the resistance value of the oil 4 reduces in association with the deterioration of the oil 4. For example, in the case of engine oil, a long-term use causes the interfusion of impurities such as carbon and metal powder. For this reason, as long as the resistance value of the oil 4 can be measured, the deterioration state of the oil 4 can be obtained.

Also, when referring to the characteristics 41 and 42, it turns out that the resistance value of the oil 4 is significantly changed depending on the temperature. For this reason, it turns out that in order to determine the deterioration state on the basis of the resistance of the oil 4, it is necessary to make the determination after correcting the measured value of the resistance to suppress the influence of the temperature.

(D1) Impedance Measurement Principle

Figure 6:
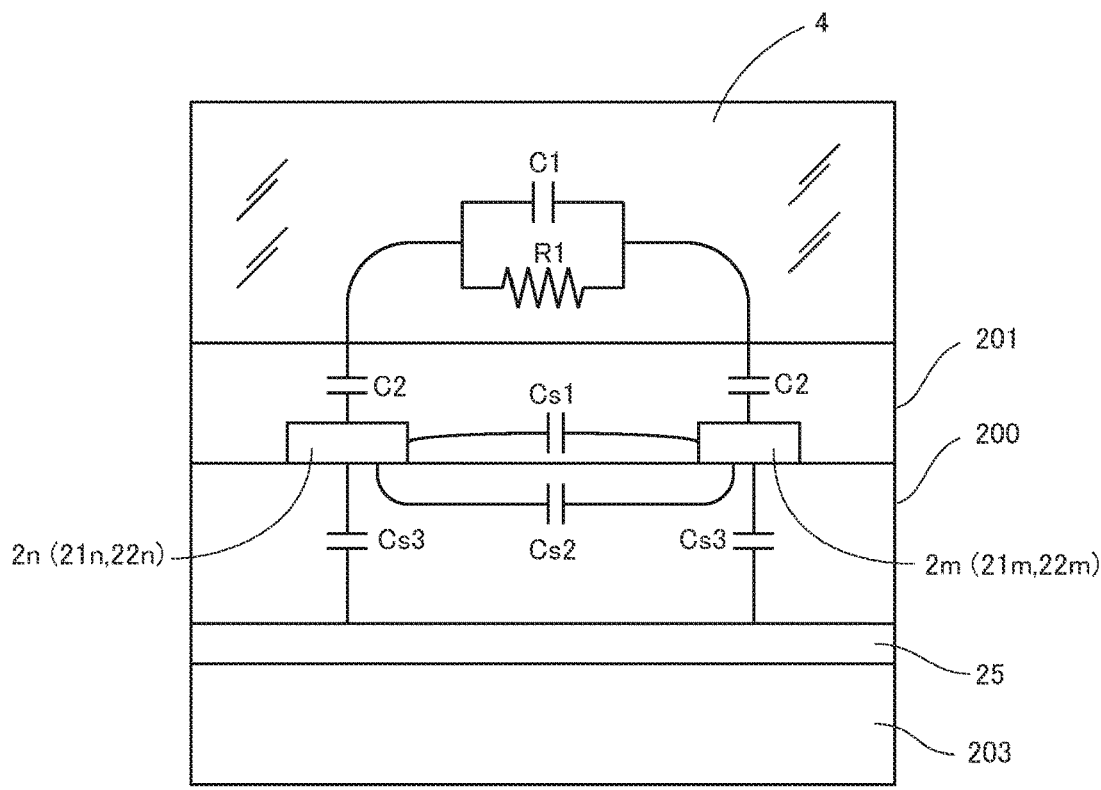
FIG. 6 is a diagram illustrating an equivalent circuit between opposite elements immersed in the oil 4.
Figure 7:
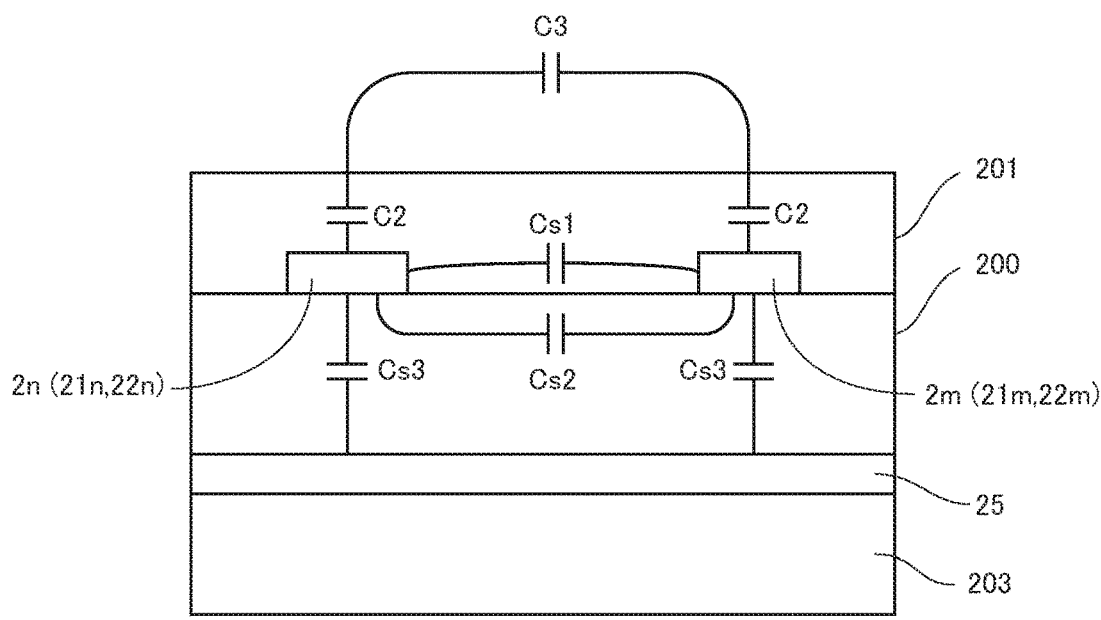
FIG. 7 is a diagram illustrating an equivalent circuit between opposite elements not immersed in the oil 4.

FIGS. 6 and 7 are explanatory diagrams on the principle of measuring the impedance between adjacent opposite elements 2$n$ and 2$m$. FIG. 6 illustrates an equivalent circuit between the opposite elements 2$n$ and 2$m$ that are immersed in the oil 4, whereas FIG. 7 illustrates an equivalent circuit between the opposite elements 2$n$ and 2$m$ that are not immersed in the oil 4. In addition, the opposite elements 2$n$ and 2$m$ respectively refer to adjacent opposite elements 21$n$ and 21$m$ or adjacent opposite elements 22$n$ and 22$m$, and in FIGS. 6 and 7, the opposite elements 2$n$ and 2$m$ are used as generic names for both cases.

As illustrated in FIG. 6, when the adjacent opposite elements 2$n$ and 2$m$ are immersed in the oil 4, an equivalent circuit of the oil 4 around the opposite elements 2$n$ and 2$m$ is a parallel circuit of capacitance C1 and resistance R1. Both ends of the parallel circuit are respectively connected to the opposite elements 2$n$ and 2$m$ via the capacitance C2 of the protective film 201. Also, between the opposite elements 2$n$ and 2$m$, parasitic capacitance Cs1 through the protective film 201, parasitic capacitance Cs2 through the base material 200, and parasitic capacitance Cs3 through the base material 200 and the ground plate 25 are present. Given that the sum of these parasitic capacitances Cs1 to Cs3 is parasitic capacitance Cs, the impedance Z between the opposite elements 2$n$ and 2$m$ can be expressed by Expression (1) below.

$$Z = \left( \frac{R1}{1 + j\omega C1 \cdot R1} + \frac{2}{j\omega C2} \right) // \frac{1}{j\omega Cs} \quad (1)$$

In addition, the symbol // represents a parallel connection operator.

When the frequency f($=\omega/2\pi$) has a sufficiently large value, Expression (1) above can be approximated as Expression (2) below. Expression (2) below does not include the resistance R1 of the oil 4. That is, by supplying AC current having a sufficiently high frequency f1 to the opposite elements 2$n$ and 2$m$ and obtaining the impedance Z as the ratio between the effective values of voltage and current at the time, the capacitance between the opposite elements 2$n$ and 2$m$ can be measured. Also, the capacitance C2 and the parasitic capacitance Cs have values not varied by the liquid level height, and therefore by measuring the capacitance between the opposite elements 2$n$ and 2$m$, the liquid level height can be obtained.

$$Z \approx \left( \frac{1}{j\omega C1} + \frac{2}{j\omega C2} \right) // \frac{1}{j\omega Cs} \quad (2)$$

On the other hand, when the frequency f has a sufficiently small value, Expression (1) above can be approximated as Expression (3) below. Expression (3) below includes the resistance R1 of the oil 4. That is, by supplying AC current having a sufficiently low frequency f2 to the opposite elements 2$n$ and 2$m$ and obtaining the impedance Z as the ratio between the effective values of voltage and current at the time, the resistance R1 between the opposite elements 2$n$ and 2$m$ can be obtained. Note that the resulting value includes an error due to the capacitance C2 and the parasitic capacitance Cs.

$$Z \approx \left( R1 + \frac{2}{j\omega C2} \right) // \frac{1}{j\omega Cs} \quad (3)$$

(D2) Resistance Value Error Compensation

As illustrated in FIG. 7, when the adjacent opposite elements 2$n$ and 2$m$ are not immersed in the oil 4, an equivalent circuit of surrounding air is capacitance C3. For this reason, the equivalent circuit between the opposite elements 2n and 2m is a circuit obtained by connecting the parasitic capacitance Cs in parallel to a circuit where the capacitance C2 of the protective film 201 is connected in series to both ends of the capacitance C3. Accordingly, the impedance Z between the opposite elements 2n and 2m can be expressed by the following expression.

$$Z = \left( \frac{1}{j\omega C3} + \frac{2}{j\omega C2} \right) // \frac{1}{j\omega Cs} \quad (4)$$

Note that the capacitance C3 of the surrounding air has a sufficiently small value as compared with the parasitic capacitance Cs of the opposite elements 2n and 2m. For this reason, Expression (4) above can be approximated as Expression (5) below.

$$Z \approx \frac{1}{j\omega Cs} \quad (5)$$

That is, by measuring the impedance Z of the opposite elements 2n and 2m not immersed in the oil 4, the parasitic capacitance Cs that is the sum of the parasitic capacitances Cs1 to Cs3 can be obtained. Accordingly, by preliminarily measuring the impedance Z of the opposite elements 2n and 2m not immersed in the oil 4, a correction of eliminating the influence of the parasitic capacitance Cs (error compensation) can be made when measuring the resistance R1 between the opposite elements 2n and 2m, and therefore the resistance R1 of the oil 4 can be accurately measured.

Figure 8:
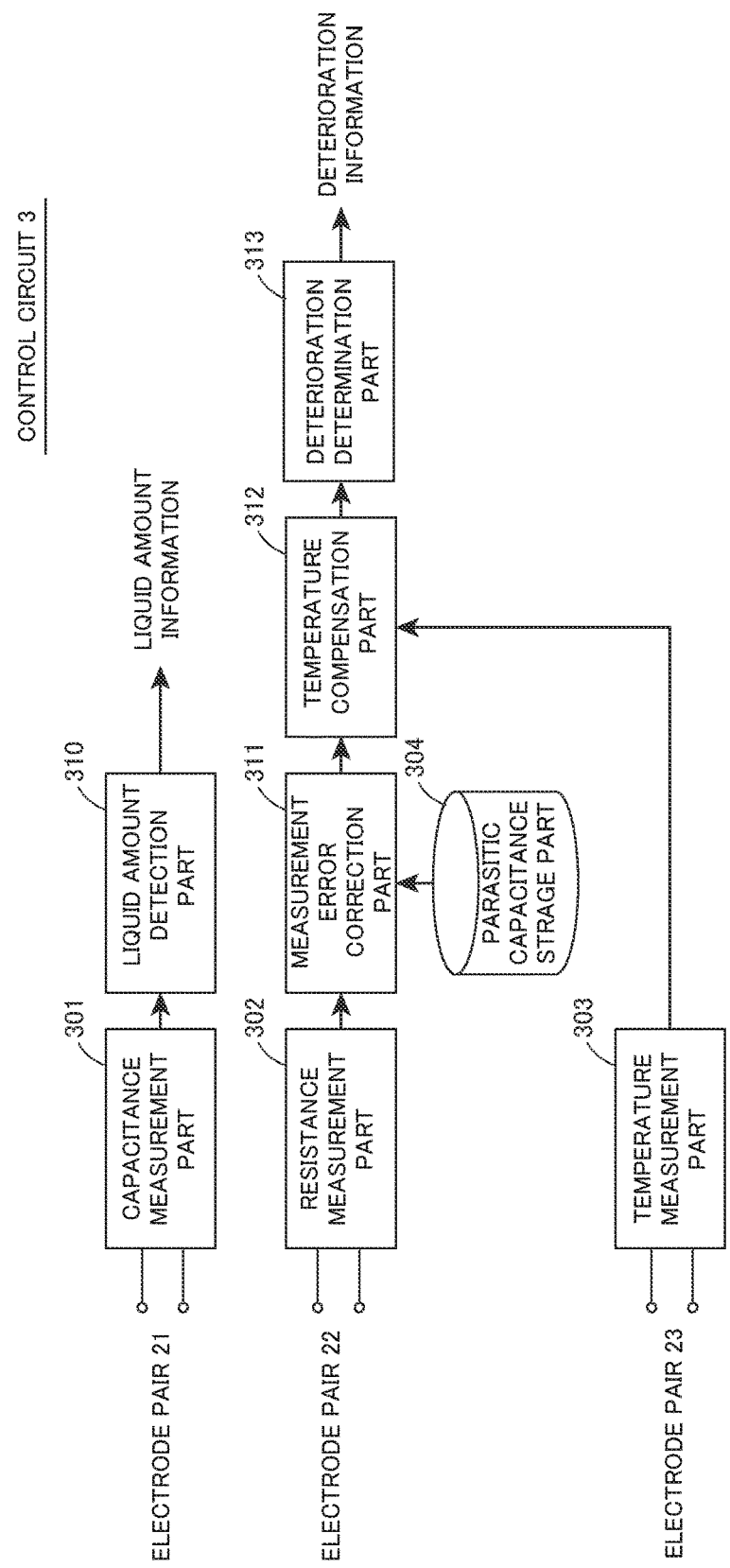
FIG. 8 is a block diagram illustrating a detailed configuration of a control circuit 3 in FIG. 1.

FIG. 8 is a block diagram illustrating a detailed configuration of the control circuit 3 in FIG. 1. The control circuit 3 detects the liquid amount of the oil 4 using the electrode pair 21, as well as determines the deterioration state of the oil 4 using the electrode pairs 22 and 23. The control circuit 3 is configured to include a capacitance measurement part 301, a resistance measurement part 302, a temperature measurement part 303, a parasitic capacitance storage part 304, a liquid amount detection part 310, a measurement error correction part 311, a temperature compensation part 312, and a deterioration determination part 313.

(E1) Capacitance Measurement Part 301

The capacitance measurement part 301 is means adapted to measure the capacitance of the electrode pair 21 in order to detect the liquid amount of the oil 4. The capacitance of the electrode pair 21 can be measured as the impedance of the electrode pair 21 at the time of supplying AC current having a predetermined frequency f1.

The impedance of the electrode pair 21 can be obtained, for example, as the ratio between the effective values of voltage and current at the time of applying AC voltage to the electrode pair 21. At this time, by selecting a sufficiently high frequency f1, the capacitance of the electrode pair 21 can be measured as the impedance in which the influence of the resistance R1 of the oil 4 is suppressed as given in Expression (2). For such capacitance measurement, a frequency f1 of 10 kHz or more can be used. For example, a frequency of 50 kHz to 1 MHz, more desirably a frequency of 100 kHz to 500 kHz is used.

(E2) Resistance Measurement Part 302

The resistance measurement part 302 is means adapted to measure the resistance value of the electrode pair 22 in order to determine the deterioration state of the oil 4. The resistance value of the electrode pair 22 can be measured as the impedance of the electrode pair 22 at the time of supplying AC current having a predetermine frequency f2.

The impedance of the electrode pair 22 can be obtained, for example, as the ratio between the effective values of voltage and current at the time of applying AC voltage to the electrode pair 22. At this time, by selecting a sufficiently low frequency f2, the resistance value R1 of the oil 4 around the electrode pair 22 can be measured as the impedance in which the influence of the capacitance C1 of the oil 4 is suppressed as given in Expression (3). For such resistance value measurement, a frequency f2 of 10 kHz or less can be used. For example, a frequency of 50 Hz to 5 kHz, more desirably a frequency of 100 Hz to 1 kHz is used.

(E3) Temperature Measurement Part 303

The temperature measurement part 303 measures the temperature of the sensor board 2 using the thermistor 23s in order to compensate for the temperature characteristic of the resistance value of the oil 4. Since the thermistor 23s is connected with the electrode pair 23, the temperature measurement part 303 detects the temperature of the oil 4 by measuring the resistance of the electrode pair 23.

(E4) Parasitic Capacitance Storage Part 304

The parasitic capacitance storage part 304 is storage means adapted to hold the parasitic capacitance Cs of the electrode pair 22. The parasitic capacitance storage part 304 holds the parasitic capacitance Cs of the electrode pair 22, which influences the measurement of the resistance value of the electrode pair 22.

For example, when the parasitic capacitance Cs of the electrode pair 22 is known, the parasitic capacitance storage part 304 holds a preliminarily given value. On the other hand, when the parasitic capacitance Cs of the electrode pair 22 is unknown, the parasitic capacitance storage part 304 holds the parasitic capacitance Cs of the electrode pair 22, which was preliminarily measured. The parasitic capacitance Cs of the electrode pair 22 varies depending on a sensor board 2, and therefore it is desirable to preliminarily measure the parasitic capacitance Cs for each sensor board 2 and store the measured parasitic capacitance Cs in the parasitic capacitance storage part 304.

The parasitic capacitance Cs of the electrode pair 22 can be measured as impedance at the time of supplying AC current having a predetermined frequency to the electrode pair 22 not immersed in the oil 4. The impedance of the electrode pair 22 can be obtained, for example, as the ratio between the effective values of voltage and current at the time of applying AC voltage to the electrode pair 22, as in the case of measuring the resistance value R1. A frequency at the time of measuring the parasitic capacitance Cs is desirably the same as the frequency f2 at the time of measuring the resistance value R1, but a different frequency can also be used.

(E5) Liquid Amount Detection Part 310

The liquid amount detection part 310 detects the liquid amount of the oil 4 in the oil tank 10 on the basis of the capacitance measured by the capacitance measurement part 301. As long as the relationship between the capacitance of the electrode pair 21 and the liquid level height of the oil 4 illustrated in FIG. 4 is preliminarily given, the liquid level height can be obtained from the measured capacitance, and the liquid level height is outputted as liquid amount information.

(E6) Measurement Error Correction Part 311

The measurement error correction part 311 corrects the measurement error of the resistance measurement part 302 using the parasitic capacitance Cs of the electrode pair 22 held by the parasitic capacitance storage part 304, and suppresses the influence of the parasitic capacitance Cs of the electrode pair 22 included in a corresponding measured value.

As given in Expression (3), in the measured value of the resistance measurement part 302, the influence of the capacitance C1 of the oil 4 connected in parallel to the resistance value R1 of the oil 4 is suppressed by using a low frequency f2, but the influence of the capacitance C2 of the protective film 201 and the parasitic capacitance Cs of the electrode pair 22 is exerted. For this reason, by correcting the measured value of the resistance measurement part 302 using the parasitic capacitance Cs of the electrode pair 22 held in the parasitic capacitance storage part 304, the influence of the parasitic capacitance Cs of the electrode pair 22 can be suppressed and the resistance value R1 of the oil 4 can be more accurately obtained.

(E7) Temperature Compensation Part 312

The temperature compensation part 312 corrects the measured value of the resistance measurement part 302 to suppress the influence of the temperature characteristics of the oil 4 on the basis of the measured value of the temperature measurement part 303. That is, the temperature compensation part 312 compensates for a change in the resistance value R1 of the oil 4 due to the temperature. This temperature compensation is desirably made for a value after the correction by the measurement error correction part 311.

(E8) Deterioration Determination Part 313

The deterioration determination part 313 determines the deterioration state of the oil 4 on the basis of the parasitic capacitance Cs and the resistance value R1 after the temperature correction. For example, the deterioration determination part 313 determines the deterioration state by comparing the corrected resistance value R1 with a threshold value, and outputs the determined deterioration state as deterioration information. The deterioration information may be binary information indicating the presence or absence of the deterioration or ternary or more information indicating the degree of the deterioration.

Second Embodiment

In the above-described embodiment, the sensor board 2 provided with the thermistor 23s is described. On the other hand, in the present embodiment, an example of the sensor board 2 provided with the wiring electrode 24 for temperature measurement will be described.

Figure 9:
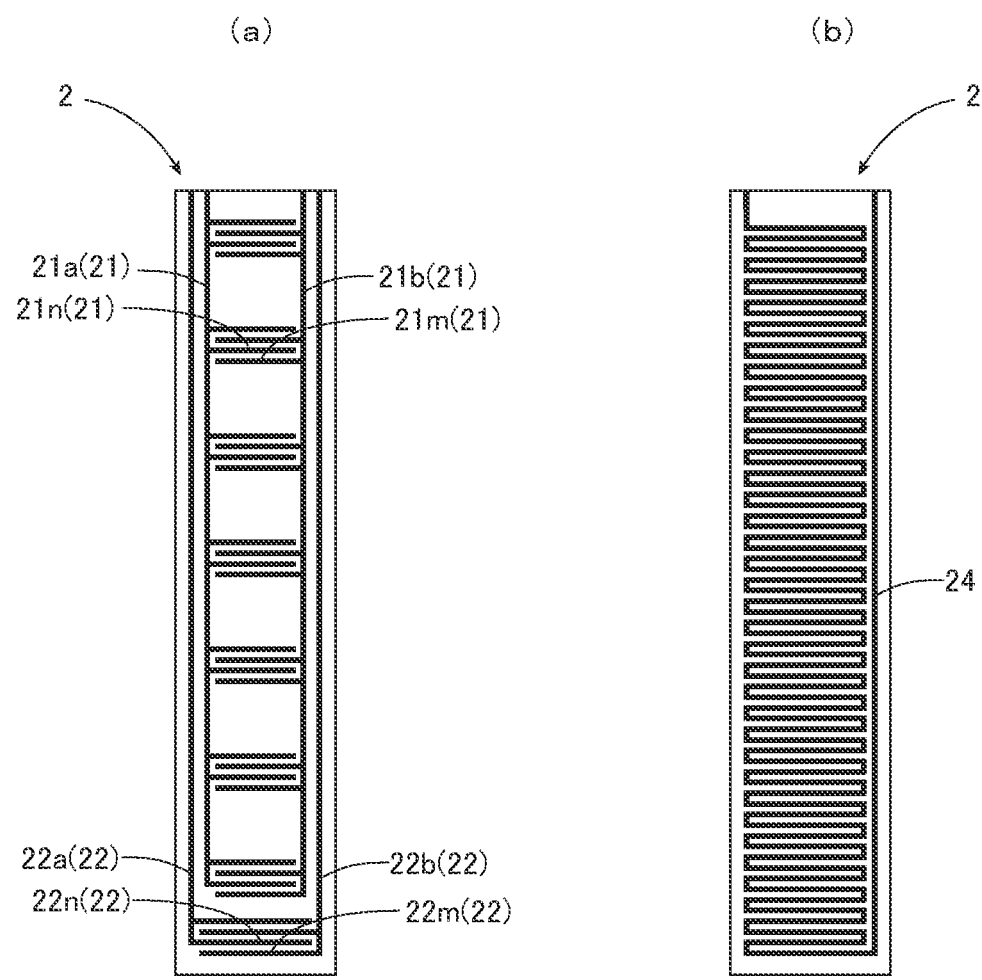
FIG. 9 is a diagram illustrating a configuration example of a sensor board 2 according to a second embodiment of the present invention.
Figure 10:
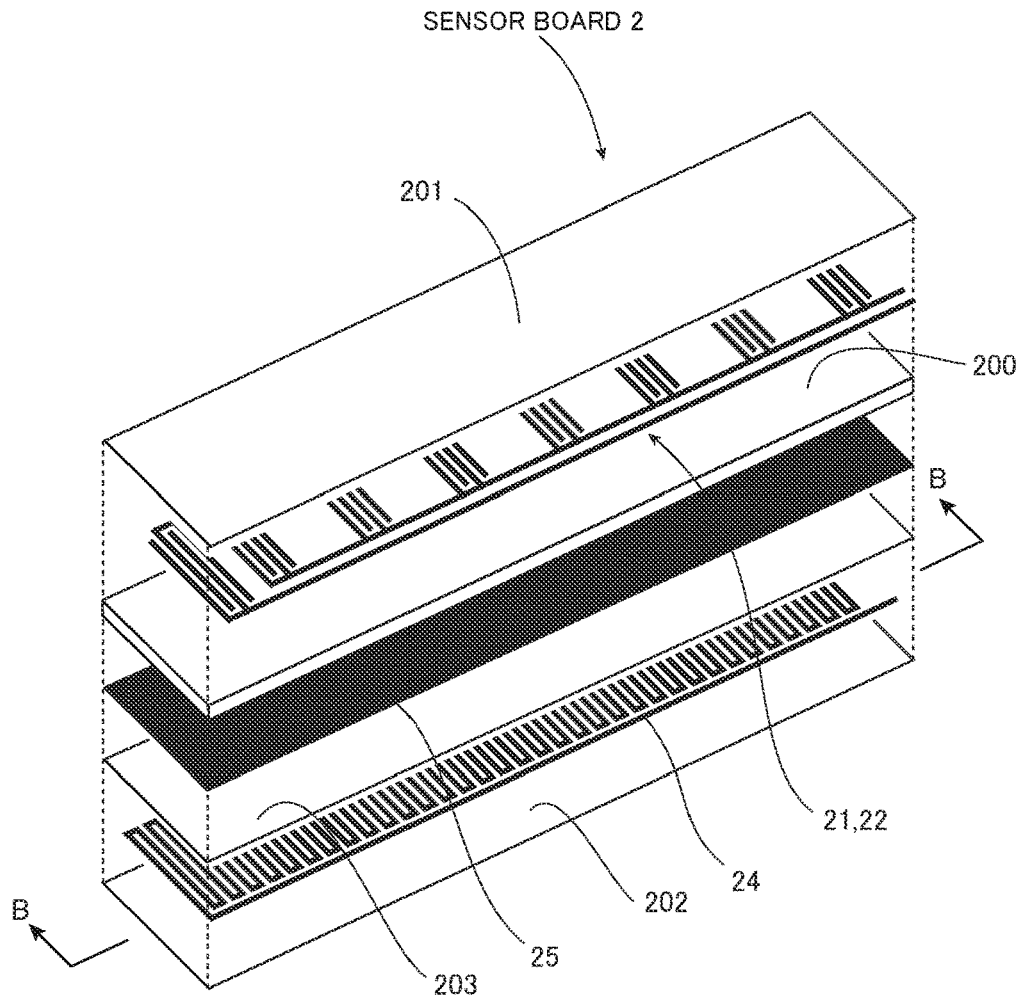
FIG. 10 is a development perspective view illustrating the structure of the sensor board 2 in FIG. 9.
Figure 11:
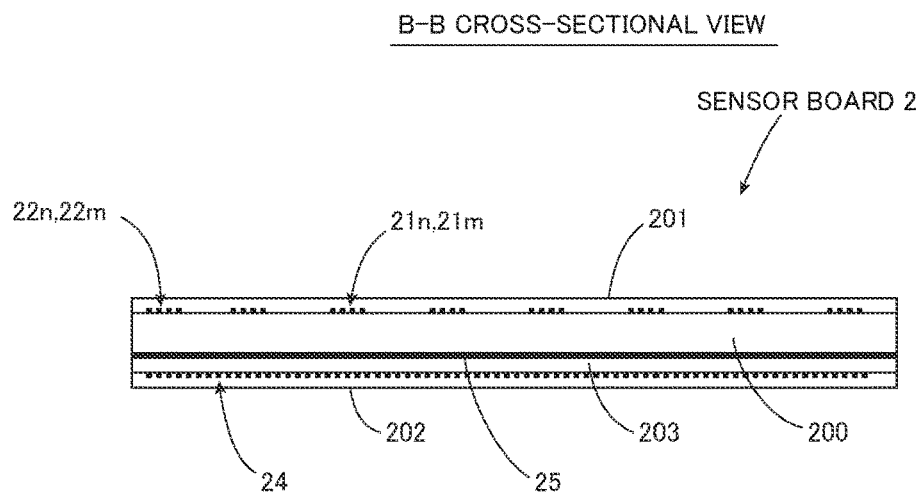
FIG. 11 is a cross-sectional view when cutting the sensor board 2 along a B-B section line in FIG. 10.

FIGS. 9 to 11 are diagrams illustrating a configuration example of the sensor board 2 according to the second embodiment of the present invention. FIG. 9(a) illustrates one principal surface (first surface) of the sensor board 2, and FIG. 9(b) illustrates the other principal surface (second surface). Also, FIG. 10 is a development perspective view illustrating the structure of the sensor board 2 in FIG. 9. FIG. 11 is a cross-sectional view when cutting the sensor board 2 along a B-B section line in FIG. 10.

When comparing the sensor board 2 in FIGS. 9 to 11 with the sensor board 2 in FIGS. 1 to 3 (first embodiment), the former is different from the latter in that the first surface is not provided with the electrode pair 23 and the thermistor 23s, but the second surface is provided with the wiring electrode 24. Also, the former is different from the latter in that a protective film 202 is formed on the second surface. In addition, the same components as those of the sensor board 2 in FIGS. 1 to 3 are marked with the same symbols and redundant description will be omitted.

On the first surface of the sensor board 2, the electrode pairs 21 and 22 are formed, and the protective film 201 covering the entire first surface is formed. On the second surface of the sensor board 2, the wiring electrode 24 is formed and the protective film 202 covering the entire second surface is formed.

(F1) Wiring Electrode 24

The wiring electrode 24 is formed as a patterned electrically conductive metal layer. For example, the wiring electrode 24 having desired pattern is formed by etching copper foil put on the second surface of the base material 200. When the ground plate 25 and the protective film 203 are formed on the second surface of the base material 200, the wiring electrode 24 is formed on the protective film 203. The wiring electrode 24 is means adapted to detect temperature by measuring resistance. That is, the temperature measurement is performed using the temperature characteristics of the resistance. For this reason, it is desirable to use a material having large temperature characteristics. Also, it is preferable to have a narrower and longer shape.

The wiring electrode 24 illustrated in FIGS. 9 to 10 have a substantially uniform line width and have a shape arranged using substantially the entire second surface of the base material 200. Specifically, the wiring electrode 24 has a pattern that extends from one end side to the other end side along the longer direction of the sensor board 2 while meandering in a reciprocating manner along the shorter direction of the sensor board 2, and after reaching the vicinity of the other end, returns toward the one end side along the longer direction of the sensor board 2. By forming such a wiring electrode 24 for temperature measurement on the second surface of the base material 200, the need for the thermistor 23s can be eliminated to suppress manufacturing cost.

(F2) Protective Film 202

The protective film 202 is a film formed on the second surface of the base material 200, and made of a dielectric material having corrosion resistance, such as a fluorine resin. The protective film 202 is formed on the entire second surface of the base material 200 and covers the wiring electrode 24. For this reason, the wiring electrode 24 is sealed by the base material 200 and the protective film 202, and does not contact with the oil 4 or air, and therefore the wiring electrode 24 can be prevented from being deteriorated and damaged by corrosion or the like. In addition, both surfaces of the base material 200 are covered with the protective films 201 and 202 of the same type, and thereby manufacturing cost can be suppressed.

Figure 12:
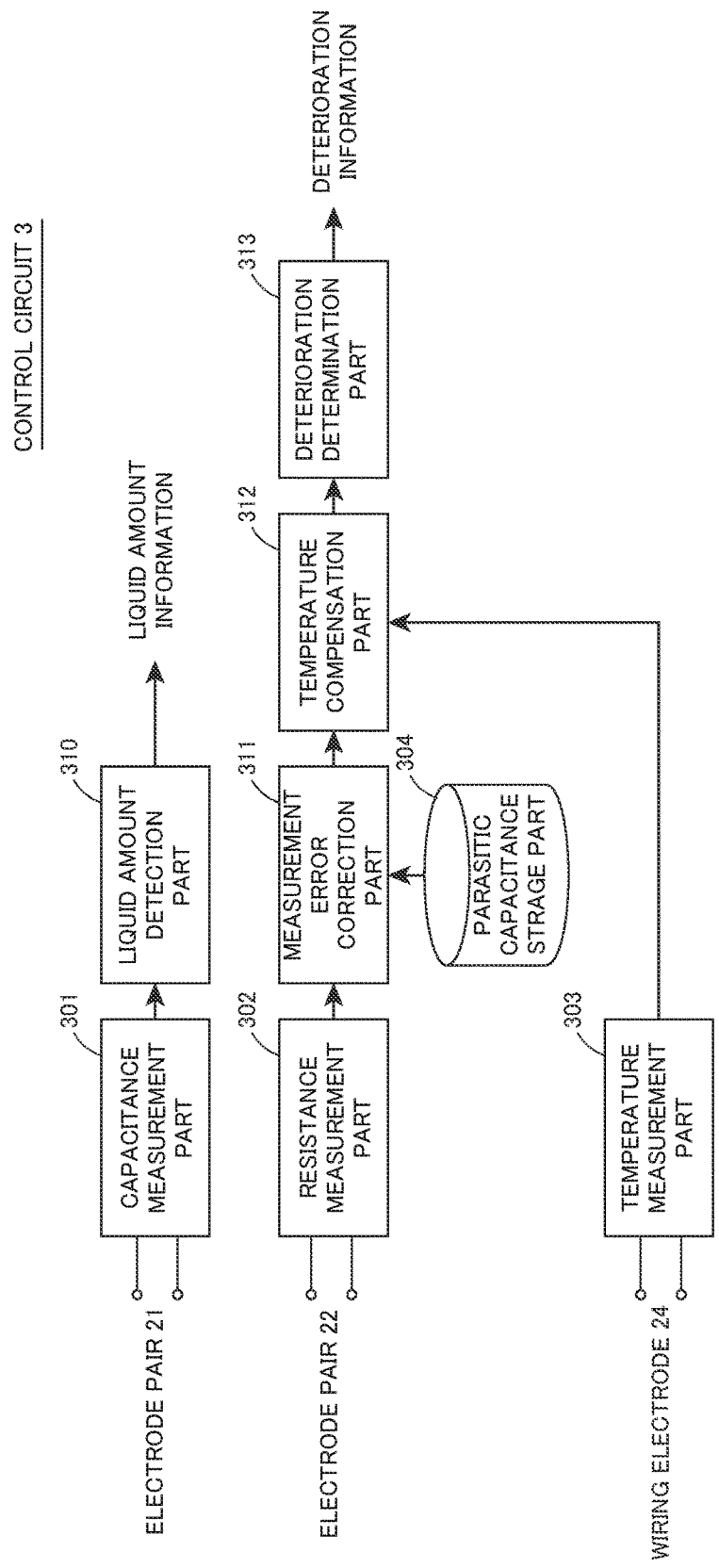
FIG. 12 is a block diagram illustrating a configuration example of a control circuit 3 according to the second embodiment of the present invention.

FIG. 12 is a block diagram illustrating a configuration example of a control circuit 3 according to the second embodiment of the present invention. When comparing the control circuit 3 in FIG. 12 with the control circuit 3 in FIG. 8 (first embodiment), the former is different from the latter in that a temperature control part 303 is connected with the wiring electrode 24. In addition, the same components as those of the control circuit 3 in FIG. 8 are marked with the same symbols and redundant description will be omitted.

(F3) Temperature Measurement Part 303

The temperature measurement part 303 detects the temperature of the oil 4 by measuring the resistance of the wiring electrode 24.

(F4) Another Pattern Example

Figure 13:
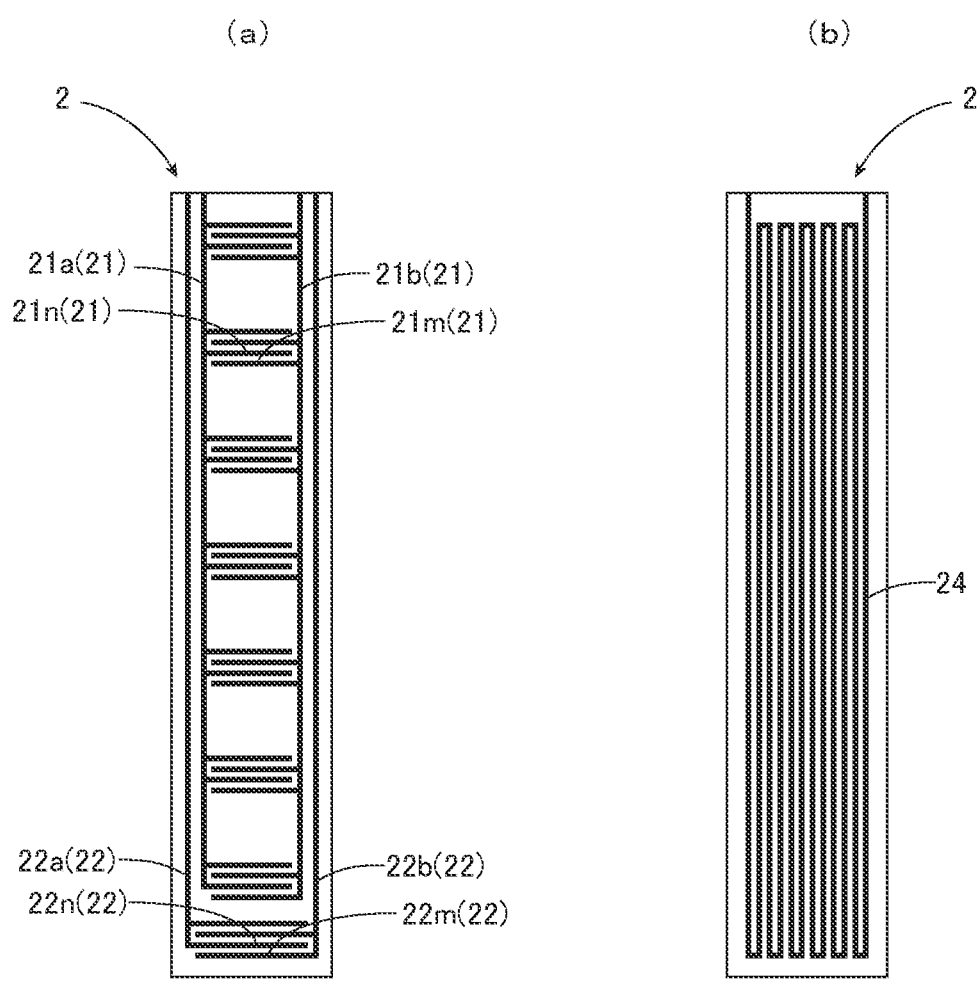
FIG. 13 is a diagram illustrating another configuration example of the sensor board 2 according to the second embodiment of the present invention.

FIG. 13 is a diagram illustrating another configuration example of the sensor board 2 according to the second embodiment of the present invention. FIG. 13(a) illustrates the first surface of the sensor board 2, and FIG. 13(b) illustrates the second surface of the sensor board 2.

When comparing the sensor board 2 in FIG. 13 with the sensor board 2 in FIG. 9 (second embodiment), only the pattern of the wiring electrode 24 is different. In addition, the rest of the configuration is the same, and therefore redundant description will be omitted.

The wiring electrode 24 illustrated in FIG. 13 has a substantially uniform line width, and has a shape arranged using the substantially entire second surface of the base material 200. Specifically, the wiring electrode 24 has a pattern that extends from one end side to the other end side along the shorter direction of the sensor board 2 while meandering in a reciprocating manner along the longer direction of the sensor board 2. By forming such a wiring electrode 24 for temperature measurement on the second surface of the base material 200, the need for the thermistor 23s can be eliminated to suppress manufacturing cost.

Third Embodiment

In the above-described second embodiment, the liquid sensor device that, with the sensor board 2 provided with the two electrode pairs 21 and 22, measures the capacitance of the electrode pair 21 to detect the liquid amount, and measures the resistance value of the electrode pair 22 to determine the deterioration is described. On the other hand, in the present embodiment, an example of a liquid sensor device that, with a sensor board 2 provided with one electrode pair 21, measures the capacitance and resistance value of the electrode pair 21 to detect a liquid amount and determine deterioration will be described.

Figure 14:
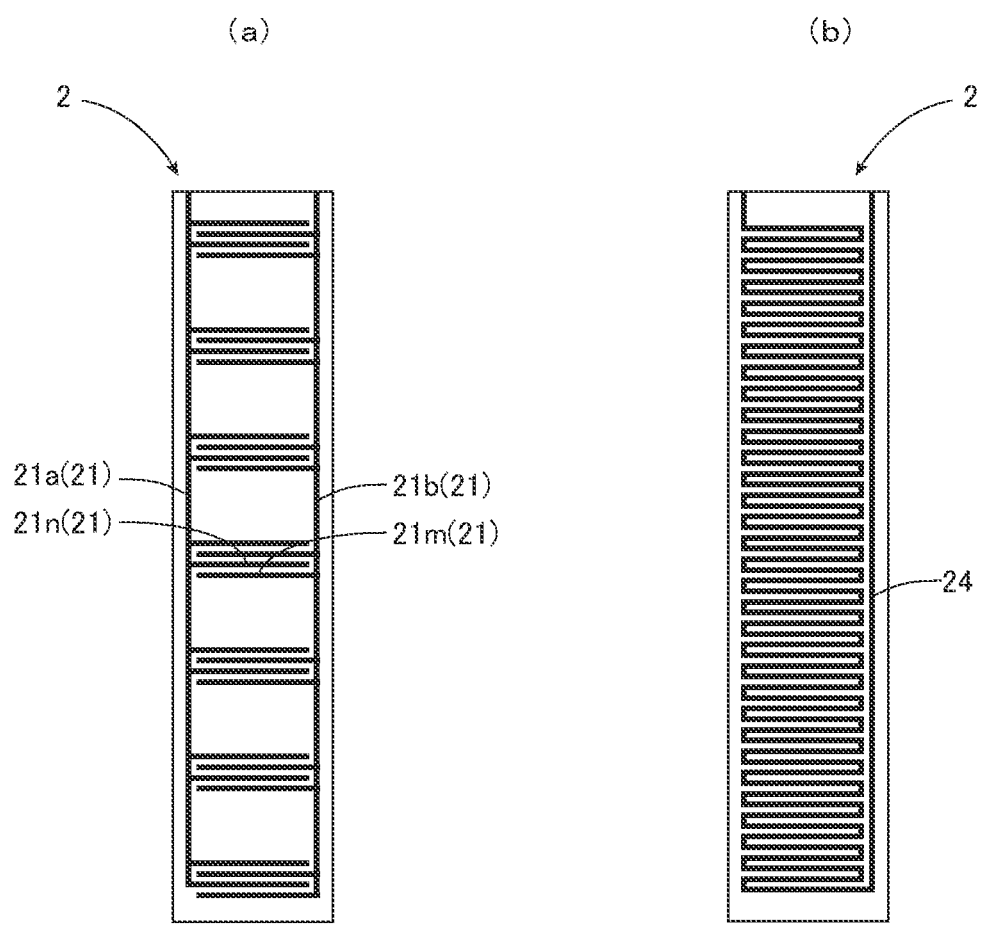
FIG. 14 is a diagram illustrating a configuration example of a sensor board 2 according to a third embodiment of the present invention.

FIG. 14 is a diagram illustrating a configuration example of the sensor board 2 according to the third embodiment of the present invention. FIG. 14(a) illustrates one principal surface (first surface) of the sensor board 2, and FIG. 14(b) illustrates the other principal surface (second surface).

When comparing the sensor board 2 in FIG. 14 with the sensor board 2 in FIG. 9 (second embodiment), the former is different from the latter in that the first surface is not provided with the electrode pair 22. In addition, the same components as those of the senor board 2 in FIG. 9 are marked with the same symbols, and redundant description will be omitted. The electrode pair 21 is one whose capacitance is measured to detect the liquid amount and whose resistance value is measured to determine the deterioration state. For this reason, the need for the electrode pair 22 can be eliminated to further suppress manufacturing cost. Also, the electrode pair 21 can be arranged extending to the vicinity of the bottom surface of the oil tank 10, and therefore a detectable liquid amount range can be expanded.

Figure 15:
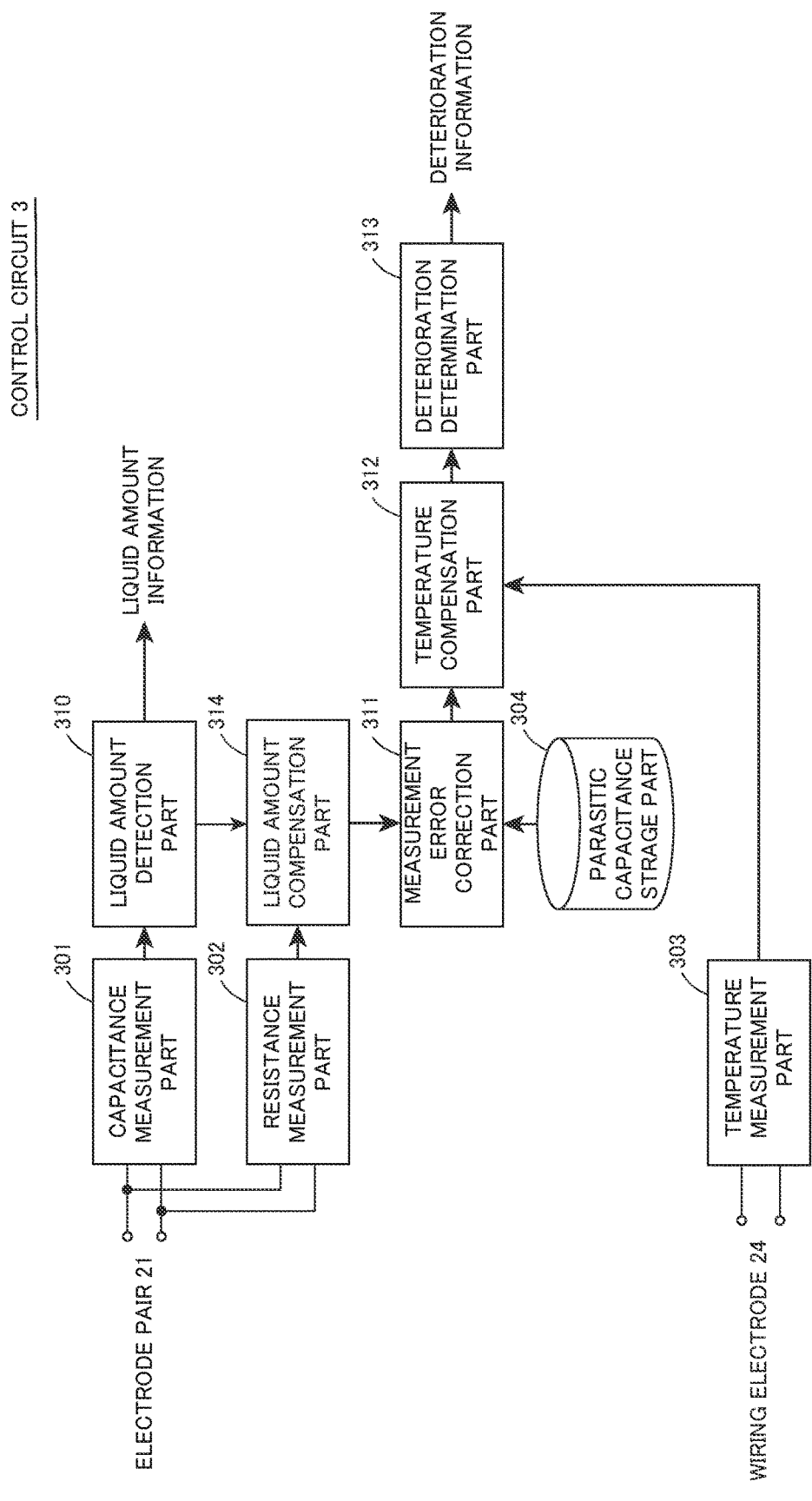
FIG. 15 is a block diagram illustrating a configuration example of a control circuit 3 according to the third embodiment of the present invention.

FIG. 15 is a block diagram illustrating a configuration example of a control circuit 3 according to the third embodiment of the present invention. When comparing the control circuit 3 in FIG. 15 with the control circuit 3 in FIG. 12 (first embodiment), the former is different from the latter in that a resistance measurement part 302 is connected with the electrode pair 21 and a liquid amount compensation part 314 is added. In addition, the same components as those of the control circuit 3 in FIG. 12 are marked with the same symbols, and redundant description will be omitted.

(G1) Resistance Measurement Part 302

The resistance measurement part 302 is means adapted to measure the resistance value of the electrode pair 21 in order to determine the deterioration state of oil 4. The resistance value of the electrode pair 21 can be measured as the impedance of the electrode pair 21 at the time of supplying AC current having a predetermined frequency f2. A method for measuring the impedance is the same as in the case of the electrode pair 22.

(G2) Liquid Amount Compensation Part 314

The liquid amount compensation part 314 corrects the measured value of the resistance measurement part 302 on the basis of the liquid amount from the liquid amount detection part 310, and suppresses the influence of the liquid amount on the measured value of the resistance measurement part 302. The electrode pair 21 for detecting the liquid amount has a shape extending in the vertical direction, and when a liquid level rises, the number of opposite elements 21n and 21m immersed in the oil 4 is increased. For this reason, even when the resistivity of the oil 4 is constant, the resistance value of the electrode pair 21 is changed depending on the liquid amount.

Figure 16:
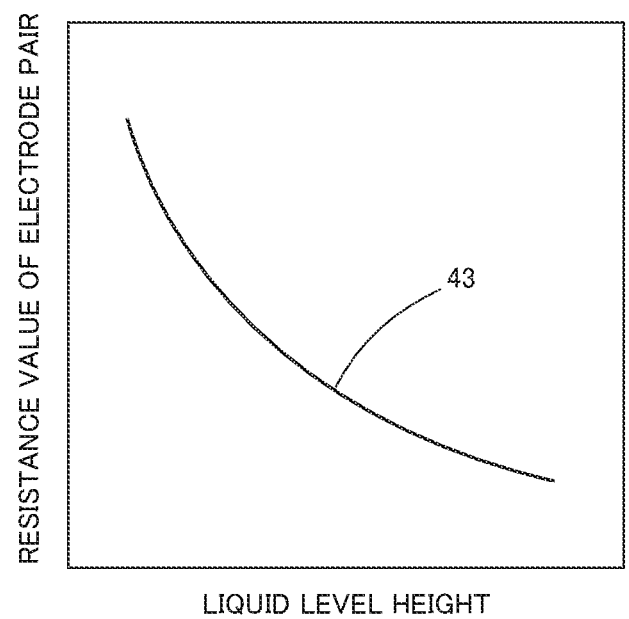
FIG. 16 is a diagram illustrating an example of the relationship between liquid level height and the resistance value of an electrode pair 21.

FIG. 16 is a diagram illustrating an example of the relationship between the liquid level height of the oil 4 and the resistance value of the electrode pair 21. This diagram is one represented with the liquid level height of the oil 4 in the oil tank 10 taken as the horizontal axis and the resistance value R1 of the electrode pair 21 taken as the vertical axis. A characteristic 43 in the diagram exhibits a downward-sloping hyperbola. That is, it turns out that the resistance value of the electrode pair 21 is decreased depending on the liquid level height of the oil 4, and both have a substantially inversely proportional relationship.

As described above, when the oil 4 is deteriorated after a long-term use, the resistivity of it reduces. For this reason, if the number of opposite elements 21n and 21m immersed in the oil 4 is constant, the deterioration state of the oil 4 can be determined on the basis of the resistance value of the electrode pair 21. However, the resistance value of the electrode pair 21 is changed depending on the liquid amount even when the resistivity of the oil is constant. Therefore, in order to determine the deterioration state of the oil 4, it is necessary to correct the resistance value on the basis of the liquid amount and correct the influence of the liquid amount. The liquid amount compensation part 314 corrects the resistance value of the electrode pair 21 measured by the resistance measurement part 302 on the basis of the liquid amount detected by the liquid amount detection part 310, and obtains the resistance value from which the influence of the liquid amount is removed. The resistance value obtained in this manner is inputted to the measurement error correction part 311.

In the above-described embodiments, the examples of the oil sensor device 1 targeting the oil 4 for detection are described, however the application target of the present invention is not limited only to such a device. That is, the present invention is applicable to a liquid sensor device targeting any liquid for detection. For example, the present invention is also applicable to a device targeting a fuel such as gasoline or light oil for detection. Further, the present invention is also applicable to a sensor device that targets a medium having fluidity other than liquid, for example, a deformable medium such as powder, grain, or gel for measurement, and measures the capacitance of the medium to measure a medium amount, as well as measures the resistance of the medium to determine the properties of the medium. Still further, the present invention can also target, for measurement, a medium whose dielectric constant or resistivity is changed depending on some condition regardless of the amount or properties of the medium, and sense an arbitrary state of the medium by measuring a change in the capacitance or resistance of the medium.

Also, in the above-described embodiments, the examples of the device that determines the deterioration state of a detection target are described. However, the present invention is not limited only to such cases. The present invention is applicable to a device that determines an arbitrary property of a detection target. For example, the present invention is also applicable to a device that determines changes in the composition and characteristics of a detection target.

REFERENCE SIGNS LIST 1 oil sensor device
2 sensor board
2n, 2m opposite element
200 base material
201-203 protective film
21 electrode pair
21a, 21b electrode
21n, 21m opposite element
22 electrode pair
22a, 22b electrode
22n, 22m opposite element
23 electrode pair
23a, 23b electrode
23s thermistor
24 wiring electrode
25 ground plate
3 control circuit
301 capacitance measurement part
302 resistance measurement part
303 temperature measurement part
304 parasitic capacitance storage part
310 liquid amount detection part
311 measurement error correction part
312 temperature compensation part
313 deterioration determination part
314 liquid amount compensation part
4 oil
C1 capacitance of oil
C2 capacitance of protective film
C3 capacitance of air
Cs, Cs1-Cs3 parasitic capacitance
R1 resistance of oil

What is claimed is:

1. A sensor device comprising:
a first electrode pair that is formed on a board and covered by an insulating protective film;
a resistance measurement part that supplies AC current to said first electrode pair to measure a resistance value of a medium around said first electrode pair;
a storage part that holds parasitic capacitance, the parasitic capacitance being between said first electrode pair; and
a property determination part that, on a basis of said resistance value and said parasitic capacitance, determines a property of said medium.

2. The sensor device according to claim 1, comprising a measurement error correction part that, on a basis of said parasitic capacitance, corrects a measurement error of said resistance value, wherein
said property determination part determines the property of said medium on a basis of said resistance value after the correction.

3. The sensor device according to claim 1, wherein said resistance measurement part measures impedance of said first electrode pair at a time of supplying AC current having a frequency of 5 kHz or less.

4. The sensor device according to claim 1, wherein said parasitic capacitance has a value measured as impedance of said first electrode pair at a time of supplying the AC current to said first electrode pair that is not close to said medium.

5. The sensor device comprising according to claim 1:
a medium container tank in which the board is arranged;
a capacitance measurement part that supplies AC current having a first frequency to said first electrode pair to measure capacitance of said first electrode pair;
a medium amount detection part that, on a basis of the capacitance measured by said capacitance measurement part, detects a medium amount in said container tank; and
a medium amount compensation part that, on a basis of said medium amount, corrects said resistance value; wherein
said first electrode pair extends in a direction intersecting with a horizontal direction;
said resistance measurement part supplies AC current having a second frequency different from the first frequency to said first electrode pair to measure a resistance value of a medium around the first electrode pair; and
said property determination part determines a property of said medium on a basis of said resistance value after the correction and said parasitic capacitance.

6. The sensor device comprising according to claim 1:
a medium container tank in which the board is arranged;
a second electrode pair that is formed on the board, arranged above the first electrode pair, and extends in a direction intersecting with a horizontal direction;
a capacitance measurement part that measures capacitance of said second electrode pair; and
a medium amount detection part that, on a basis of the capacitance measured by said capacitance measurement part, detects a medium amount in said container tank; wherein
said protective film covers said first electrode pair and said second electrode pair;
said resistance measurement part supplies AC current to said first electrode pair to measure a resistance value of a medium around said first electrode pair; and
said storage part holds parasitic capacitance of said first electrode pair.

7. The sensor device according to claim 5, further comprising
a measurement error correction part that, on a basis of said parasitic capacitance, corrects a measurement error of said resistance value, wherein
said property determination part determines the property of said medium on a basis of said resistance value after the correction.

8. The sensor device according to claim 1, comprising:
a temperature measurement part that measures temperature of said board; and
a temperature compensation part that, on a basis of said temperature, corrects said resistance value, wherein
said property determination part determines the property of said medium on a basis of said resistance value after the correction.

9. The sensor device according to claim 8, wherein said temperature measurement part obtains the temperature of said board by measuring a resistance value of an electrode formed on said board.

10. The sensor device according to claim 9, wherein said electrode is covered by said protective film.

11. The sensor device according to claim 1, wherein
said medium is liquid, and
said property determination part determines a deterioration state of said liquid.

12. The sensor device according to claim 11, wherein
said liquid is oil, and
said property determination part determines a deterioration state of said oil.

* * * * *